United States Patent [19]

Watanabe

[11] 4,107,302
[45] Aug. 15, 1978

[54] NOVEL AQUEOUS INSECTICIDAL CONCENTRATE COMPOSITION

[75] Inventor: Hiroshi Watanabe, Takasago, Japan

[73] Assignees: Osaka Kasei Company Limited, Osaka; Nippon Kayaku Kabushiki Kaisha, Tokyo, both of Japan

[21] Appl. No.: 742,100

[22] Filed: Nov. 16, 1976

[51] Int. Cl.$^2$ .............................................. A01N 9/36
[52] U.S. Cl. ..................................... 424/200; 424/210; 424/213; 424/216; 424/218; 424/225; 424/270; 424/317
[58] Field of Search ............... 424/200, 213, 225, 270, 424/358

[56] References Cited

U.S. PATENT DOCUMENTS

| | | | |
|---|---|---|---|
| 3,683,078 | 8/1972 | Haus | 424/213 |
| 3,903,273 | 9/1975 | Mast | 424/213 |

FOREIGN PATENT DOCUMENTS 1,446,771  10/1976  United Kingdom.

*Primary Examiner*—V. D. Turner
*Attorney, Agent, or Firm*—Lane, Aitken, Dunner & Ziems

[57] ABSTRACT

A novel aqueous insecticidal concentrate composition comprising (a) an insecticidal organo-phosphorus compound, (b) water and (c) a surface active agent in an amount sufficient to render the organo-phosphorus compound soluble in the water, the pH of the composition being in the range of 3.0 to 8.5.

6 Claims, No Drawings

NOVEL AQUEOUS INSECTICIDAL CONCENTRATE COMPOSITION

BACKGROUND OF THE INVENTION

This invention relates to a novel aqueous insecticidal concentrate composition. The term "insecticidal concentrate composition" used herein is intended to mean a solution, such as an emulsifiable concentrate, which contains insecticidal compound preferably in a concentration as high as 2% or more and is practically-applied after dilution with water to a concentration of below 1%.

An aqueous pesticidal concentrate composition containing a triazine derivative, a pyridine derivative, a chlorinated hydrocarbon or others as a pesticidal compound is disclosed in British Pat. No. 1,446,771. However, the British Patent does not disclose an aqueous insecticidal concentrate composition containing an insecticidal organo-phosphorus compound as an active compound. An insecticidal organo-phosphorus compound in such known aqueous pesticidal concentrate composition in which the active compound is dispersed in water in the form of a finely divided solid is very unstable and decomposes with the lapse of time.

Accordingly, an aqueous insecticidal concentrate composition containing an insecticidal organo-phosphorus compound is unknown.

Known concentrate compositions containing an insecticidal organo-phosphorus compounds are generally composed of an insecticidal organo-phosphorus compound, an organic solvent, a surface active agent and a stabilizer. Water is scarcely contained in the compositions (e.g., the water content is generally below 1%). This is because organo-phosphorus compounds which serve as insecticide are usually poor in stability when water is present. Accordingly, it has been heretofore considered that the presence of water in the phosphorus compound-containing concentrate composition which is essentially required to have relatively long shelf life must be avoided.

Almost all of the organic solvents employed in the known concentrate compositions for agriculture or epidemic prevention, such as emulsifiable concentrates have more or less toxity against animals and plants and take part in air or water pollution leading to many evils when used as insecticides. Further, the organic solvents employed in conventional insecticidal concentrate compositions are ordinarily combustible and have a danger of taking fire, so that the insecticidal concentrate compositions using such combustible organic solvents and containing no water must be handled or stored with the utmost care. Accordingly, use of water instead of organic solvents is very convenient from every point of view. In addition, organic solvents which have been used in insecticides are important as starting materials for the synthesis of useful compounds or energy sources. In the sense, the replacement of organic solvents by water is favorable from a social point of view.

SUMMARY OF THE INVENTION

It is accordingly, an object of the present invention to provide a stable aqueous insecticidal concentrate composition containing an insecticidal organo-phosphorus compound and having less toxicity than known emulsifiable concentrate composition containing same compound.

It is another object of the present invention to provide an insecticidal concentrate composition which has little or no tendency to air or water pollution.

It is a further object of the present invention to provide an insecticidal concentrate composition which is advantageous in economy.

We have found that use of a surface active agent in an amount enough to render an insecticidal organo-phosphorus compound soluble in water assures, unexpectedly, formation of a stable concentrate composition using, instead of organic solvent, water having been considered to be avoided.

The present invention is based on the above finding and contemplates to provide an aqueous insecticidal concentrate composition which comprises (a) an insecticidal organo-phosphorus compound, (b) water and (c) a surface active agent in an amount enough to render the organo-phosphorus compound soluble, the pH of the composition ranging from 3.0 to 8.5. The composition is obtainable as a clear solution rather than a dispersion because the organo-phosphorus compound is entirely dissolved in the aqueous medium.

DETAILED DESCRIPTION OF THE INVENTION

There are usable in the present invention almost all insecticidal organo-phosphorus compounds other than a very few of insecticidal organo-phosphorus compounds of a type which is very rapidly decomposed upon contact with water and is thus especially unstable in water. Preferred phosphorus compounds which are sparingly soluble in water, e.g., a solubility in water of below about 2%, are expressed by the following general formula

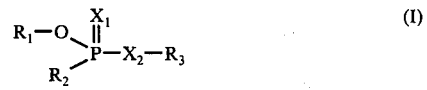

(in which $R_1$ represents a lower alkyl preferably having 1 to 3 carbon atoms, $R_2$ represents lower alkoxy preferably having 1 to 3 carbon atoms or phenyl, $R_3$ represents a phenyl group having one to three substituents selected from the group consisting of $CH_3$, $NO_2$, $CN$, $Cl$ and $-S-CH_3$, 2-isopropyl-4-methyl-6-pyrimidinyl group, 3,5,6-trichloro-2-pyridyl group, 1,2-diethoxycarbonyl group, or 1-ethoxycarbonyl-1-phenylmethyl group, and $X_1$ and $X_2$ are the same or different and are an oxygen atom or a sulfur atom).

Most preferable compounds are expressed by the following general formula

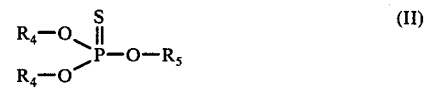

(in which $R_4$ are $CH_3-$ or $C_2H_5-$, and $R_5$ represents

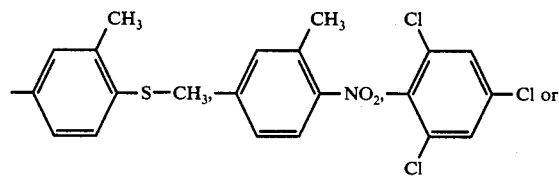

-continued

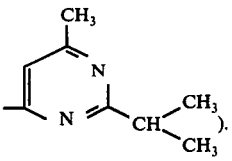

Examples of the compounds expressed by the general formulae (I) and (II) include O,O-dimethyl-O-(3-methyl-4-methylthiophenyl) thiophosphate (hereinafter referred to simply as fenthion), O,O-dimethyl-O-(3-methyl-4-nitrophenyl)thiophosphate (hereinafter referred to simply as fenitrothion),O,O-diethyl-O-[2-isopropyl-4-methylpyrimidyl (6)]thiophosphate (hereinafter referred to simply as diazinon), S-(1,2-dicarboethoxyethyl)-O, O-dimethyldithiophosphate (hereinafter referred to simply as malathion), O,O-dimethyl-O-2,4,5-trichlorophenylthiophosphate (hereinafter referred to simply as ronnel), O,O,O',O'-tetramethyl-O,O'-thiodi-P-phenylene)thiophosphate, O,O-diethyl-O-(3,5,6-trichloro-2-pyridyl)thiophosphate, O,O-dimethyl-S-[(α-ethoxycarbonyl) benxyl]dithiophosphate, O-ethyl-O-(4-nitrophenyl)-phenylphosphonothioate, O,O-dimethyl-O-(4-cyanophenyl)thiophosphate, etc. The ratio of the phosphorus compound to the concentrate composition is preferably in the range of 2 to 50%.

The amount of water in the concentrate composition of the present invention is variable according to the content of an insecticidal organo-phosphorus compound in the concentrate composition but preferred amount is from 20% by weight to 96% by weight based on total weight of the concentrate composition. If circumstances require, the water may contain an organic solvent in an amount of less than the water. When the concentration of the insecticidal organo-phosphorus compound in the concentrate composition of the present invention exceeds 30%, it is preferred to use, in conjunction with water, an organic solvent, preferably a polar organic solvent, in an amount of below 15% based on the total weight of the concentrate composition. The polar organic solvents include ketones, cellosolve ethers, alcohols, etc. which have a boiling point of, preferably, not lower than 80° C. Suitable polar organic solvents include, for example, cyclohexanone, isophorone, ethyl cellosolve, methyl cellosolve, isopropyl cellosolve, cyclohexanol, diacetone alcohol, butanol, butyl glycol and the like. When diazinon is used as the phosphorus compound, ketones and cellosolve ethers are most preferable.

The surface active agent useful in the present invention depends on the nature of the insecticidal organic phosphorus compound. Usable surface active agents include nonionic surface active agents, ionic surface active agents and ampholytic surface active agents. Polyoxyethylene alkylallylphenyl ethers and homologues thereof are preferred due to a wide range of application.

The surface active agent should be added in an amount sufficient to make the insecticidal organo-phosphorus compound soluble in said water, and the amount varies depending on the kind and amount of insecticidal organo-phosphorus compound, and also on the kind of the surface active agent itself. In general, the preferred amount of surface active agent is in the range of 0.4 to 4 times the weight of an insecticidal organo-phorphorus compound and in the range of 2 to 30% (by weight) of the composition.

In practicing the present invention, the pH of the concentrate composition should be adjusted in the range of 3.0 to 8.5 so as to prevent the organo-phosphorus compound from being decomposed. The optimum pH of the composition varies depending on the kind of the organo-phosphorus compound. For example, with the malathion, the optimum pH is in the range of 3.0 to 4.0 with the diazinon, the pH in the range of 6.5 to 8.5 is suitable. When a number of other phosphorus compounds are used, the composition in the pH range of 5.0 to 6.5 is most stable.

When a relatively stable insecticidal material such as fenthion, ronnel or the the like is used for preparing an aqueous insecticidal concentrate composition of the present invention, the composition may often fall on a suitable range of pH only with the use of a surface active agent and water and it is not necessary to use any pH-adjusting agent. With a relatively unstable insecticidal compound such as diazinon, however, it is necessary to use a buffer solution for pH adjustment so as to suppress the change in quality of the insecticidal compound per se with a large of time. In this case, the choice of the buffer solution should depend on the nature of the insecticidal compound. With the diazinon, for example, Sorensen's buffer solution composed of an aqueous solution of potassium dihydrogenphosphate and an aqueous solution of disodium hydrogenphosphate, Kolthhoff's buffer solution composed of an aqueous solution of potassium dihydrogenphosphate and an aqueous solution of borax or McIlvaine's buffer solution composed of an aqueous solution of disodium hydrogenphosphate and an aqueous solution of citric acid is suitable for the pH adjustment.

In some cases, the aqueous insecticidal concentrate composition of the present invention may advantageously be improved in stability by addition of stabilizers. Any epoxy compound is a suitable stabilizer for the aqueous insecticidal concentrate composition of the present invention. The epoxy compounds are for example, epichlorohydrin, butyl glycidyl ether, phenyl glycidyl ether, cresyl glycidyl ether, methacrylic acid glycidyl ether, ethylene glycol glycidyl ether, propylene glycol glycidyl ether, polyethylene glycol diglycidyl ether, polypropylene glycol diglycidyl ether, butandiol diglycidyl ether, glycerol diglycidyl ether, etc. These stabilizers are usually added in an amount of 0.5 to 3% by weight of a final composition. Further, addition of sodium erythorbate is effective, to some extent, in improving the stability and more effective when used in combination with an epoxy compound. However, the combination is disadvantageous due to formation of coloring material.

The storage stability of the aqueous insecticidal concentrate composition of the present invention stands comparison with those of known emulsifiable concentrates using organic solvent. That is, the concentrate composition of the present invention is found to have a decomposition rate of an insecticidal organo-phosphorus compound as low as 3 to 5% when tested at room temperature (i.e., 5°-34° C) over one year.

The aqueous insecticidal concentrate composition of the present invention is similar in nature to the known emulsificable concentrate compositions and can be applied in the same manner and amount as the known compositions. In comparison with the known emulsifiable concentrates, the concentrate composition of the present invention exhibits the same or superior level of insecticidal effect to noxious insects such as larvae of mosquito, fly, midge, gnat, etc., when determined by an immersion method. Further, it has been found by a peroral test using larvae of Orthoptera and Lepidptera insects having mandibles that the concentrate composition of the present invention has the same efficacy against the agricultural noxious insects as the known counterparts. In addition, the concentrate composition of the invention is not inferior in residual efficacy to concentrates of other types. As for peroral acute toxicity, 50% — lethal doses of the concentrate composition of the present invention for mice and rats is much more by about 30 to 50% than an known emulsifiable concentrate containing the same insecticidal organo-phosphorus compound as the present invention. This means that the concentrate composition of the invention is less harmful than the known emulsifiable concentrate. With regard to the percutaneous toxicity which may present a problem upon applying an insecticide by sprinkling, neither mouse nor rat dies when the concentrate composition of the invention is dosed at a level of 50% — lethal dose or the known emulsifiable concentrate. From the above it will be clear that the composition of the invention is much less noxious. In a skinirritating test, neither irriation nor inflammation is recognized. Further, an inhalation test reveals that the concentrate composition of the invention is more harmless than known emulsifiable concentration. A fish test also reveals that the concentration of the concentrate composition of the invention required to attain the same mortality of, for example, goldfish and red killifish is about 1.5 to 2 times as great as that of an emulsion-type insecticide, thus showing an improvement in toxicity.

The reduction of toxicity of the concentrate composition of the invention is considered to result from omission or reduction in amount of organic solvent inherently possessed of toxicity and reduced synergistic toxicity of the other components due to the omission of organic solvent, and also from reduction in velocity and amount of absorption of insecticidal component through skin and mucouse membrane due to use of water as major proportion of all of solvent.

The concentrate composition of the present invention exerts on a mitigated action on plants. So far as an proper insecticidal compound is properly used depending on the kind of plant, the concentrate composition of the present invention is hard to bring about the ill effects on plant.

Further, the concentrate composition of the present invention is very conveniently used for the epidemic prevention purpose since it has little or no tendency to damage of synthetic resin articles, rubber articles and coating surfaces when compared with known emulsifiable concentrates.

The present invention will be particularly illustrated by way of the following examples, which should not be construed as limitation thereof.

EXAMPLE 1

(1) Preparation Of Insecticidal Concentrate Composition Of Invention (Hereinafter the aqueous insecticidal composition of the present invention is referred to as "aqueous concentrate")

(a) 5% fenthion aqueous concentrate 5 g of fenthion as an insecticidal organo phosphorus compound and 15 g of polyoxyethylene distyrylmethylphenyl ether (ethylene mol number = 10) as a surface active agent were gradually added to 80 g of water with stirring to obtain a uniform clear solution. The solution or preparation was adjusted to have a pH of 5 – 6.

(b) 5% fenthion emulsifiable concentrate . . . reference insecticide 5 g of fenthion, 5 g of a mixture of polyoxyethylene nonylphenyl ether and sodium dodecylbenzenesulfonate, 20 g of xylene and 70 g of kerosene were mixed together for dissolution.

(2) Comparative Test Results

The above two insecticides were tested to determine insecticidal efficacy, acute toxity and stability. The test results are shown below.

(a) Insecticidal Efficacy

| kind of insect and test method | | Present invention 5%-fenthion aqueous concentrate | Reference 5%- emulsifiable concentrate |
| --- | --- | --- | --- |
| Houseflies (larvae) | immersion method[1] LC-50 | 0.13–0.15 ppm | 0.15–0.33 ppm |
| Mosquitoes (culex pipiens) | immersion method LC-50 | 0.0018 ppm | 0.0019 ppm |
| Houseflies (adult) | filter paper contact method[2] KT-50 | 3 hrs. & 36 min. | 3 hrs. & 22 min. |
| Houseflies (adult) | spray-dropping[3] method (Nagasawa's method) KT-50 | 22 min. & 46 sec. | 18 min. & 32 sec. |
| Cockroaches (B.germanica) | plywood contact mthod KT-50[4] | 7 hrs. | 5 hrs. |

Note:
[1]Immersion method: Each 5 ml of the insecticidal solution diluted to different concentrations was placed in a tall-skirted schale (i.e., small plate) having a diameter of 9 cm and a height of 6 cm, in which 30 worms to be tested were put. Thereafter, the schale was covered and allowed to stand at about 25° C for 24 hours for determining the LC-50.
[2]Filter paper-contacting method: A schale having a diameter of 9 cm and a height of 2 cm was covered with filter paper on the bottom thereof. 0.32 ml of a 0.5% insecticidal solution was uniformly applied to the filter paper by means of a 1 ml messpipet, in which 30 worms were put. The schale was maintained at about 25° C to determine the KT-50.
[3]Spray-dropping method (Nagasawa's method): A glass cyclinder having an inner diameter of 20 cm and a height of 43 cm was covered at the top thereof with a glass plate having a circular through-hole with a diameter of 2.5 cm at the center thereof and was placed on a glass plate at the bottom thereof. Then, a test pot containing 30 worms was set in the glass cylinder. Thereafter, 0.5 ml of a 0.5% insecticidal sample solution was sprayed from the circular through-hole under a pressure of 20 lb/in (i.e., 1.5 kg/cm$^2$). 10 seconds after the spraying, the glass plate at the bottom of the cylinder was removed so as to permit the fine particles of the sprayed solution to enter the worm-containing pot. By the above procedure, the KT-50 was determined.
[4]Plywood contact method: A 0.5% insecticidal sample solution was uniformly brush applied to a plywood plate in an amount of 50 ml/m$^2$, followed by allowing the stand as it is for drying. Then, a circular glass ring having a diameter of 9 cm and a height of 6 cm was placed on the applied face in which 30 worms were let, thereby determining the KT-50.
It will be noted that the LC-50 is intended to mean 50% - lethal concentration and the KT-50 means 50% - lethal-knockdown time.

(b) Acute Toxicity

| kind of test animal and test method | | | aqueous preparation of invention | emulsion for reference |
| --- | --- | --- | --- | --- |
| peroral dose | ddy mice (male) | LD-50 | approximately 2.8 ml/kg | 2.0 ml/kg |
| " | ddy mice (female) | LD-50 | 3.6 ml/kg | 2.5 ml/kg |
| " | SD rats (male) | LD-50 | 4.98 ml/kg | 2.9 ml/kg |
| " | SD rats (female) | LD-50 | 4.16 ml/kg | 3.2 ml/kg |
| " | Wister rats (female) | LD-50 | 3.34 to 4.30 ml/kg | 2.8 ml/kg |
| percutaneous dose | ddy mice (male) | LD-50 | more than 9.93 ml/kg | 10 ml/kg |
| " | ddy mice (female) | LD-50 | more than 11.3 ml/kg | 11.3 ml/kg |
| " | Wister rats | LD-50 | approximately | |

| kind of test animal and test method | aqueous preparation of invention | emulsion for reference |
| --- | --- | --- |
| (male) | 18 ml/kg | 9.8 ml/kg |

Note: LD-50 means 50% - lethal dose. In the toxicity test, 10 mice were taken as one group and 6 to 7 groups were subjected to the test. With rats, 6 rats were taken as one group and 6 groups were used for the test. The observation was conducted for 7 days or 14 days.

The peroral toxicity was examined as follows: an insecticidal concentrate was forcibly dosed into the stomach of a test animal by the use of a metal stomach probe. While, the percutaneous toxicity was examined by shaving the back of a test animal and applying an insecticidal concentrate to the shaved back.

The percutaneous toxicity of the aqueous insecticide of the invention against the mice (male and female) was as follows: no mice died when the aqueous insecticide was dosed in amounts of 9.93 ml/kg and 11.3 ml/kg to the male and female mice, respectively, without evidencing clear toxic symptoms. From this it is assumed that the LD-50 is far greater than the above-indicated amounts.

(c) Decomposition Rate Of Effective Ingredient During Storage

| storing conditions | Present invention 5% fenthion concentrate | Reference 5% fenthion emulsifiable concentrate |
| --- | --- | --- |
| 40° C, 4 weeks | 1.12 % | 1.03 % |
| 40° C, 8 weeks | 2.63 % | 2.72 % |
| room temperature, one year (5–34° C) | 3.30 % | 3.15 % |

Note: The test was conducted by placing the sample in a hermetically sealed glass bottle and keeping the bottle in a light-shielded place of the predetermined temperature.

(3) Discussion

As for the insecticidal efficacy, the aqueous concentrate of the present invention is equivalent or rather superior to the known emulsifiable concentrate with regard to larvae of Houseflies and Mosquitoes, but the latter is superior with regard to adult of Houseflies, Mosquitoes and German cockroach. However, the insecticidal efficacy of the aqueous concentrate of the present invention is within a range enough to stamp out the noxious insects when the insecticide is applied in a standard amount.

There is little difference between the aqueous concentrate of the present invention and the known emulsifiable concentrate concerning the decomposition rate with the lapse of time. As for the acute toxicity, the aqueous concentrate of the present invention is less harmful than the known emulsifiable concentrate. Especially, the reduction in percutaneous toxicity is considerable. As a whole, the aqueous concentrate of the present invention is similar in insecticidal efficacy and stability to the known emulsifiable concentrate and has reduced toxic characteristics.

EXAMPLE 2 (Comparative Test for Residual Efficacy)

(1) Tested Insecticides
(a) Aqueous 5% fenthion aqueous concentrate prepared in the same manner as in Example 1—(1)—(a).
(b) 5% fenthion emulsifiable concentrate prepared in the same manner as in Example 1—(1)—(b).
(2) Tested insect: Adult of houseflies
(3) Test Period: July 23, 1973 —August 16, 1973
(4) Test Method: The respective concentrate were diluted ten times with water and were each sprayed over the inner surfaces of a room in an amount 50 ml/m$^2$. 1, 5, 10, 18 and 25 days after the spraying treatment, each 200 flies were let in the room and the room was closed. 24 hours after the closing, the number of dead flies was examined. In the test results, the term "closed division" is intended to mean that the windows in the room were all closed during the course of the test, while the term "opened division" means that the windows were all opened during a period between an examined day and a next letting-in day.
(5) Test Results Mortality (%) in a day in closed division

| | examined date | 7/23–7/24 | 7/27–7/28 | 8/1–8/2 | 8/9–8/10 | 8/16–8/17 |
| --- | --- | --- | --- | --- | --- | --- |
| Present invention | 5% fenthion aqueous concentrate | 100 | 100 | 100 | 100 | 100 |
| Reference | 5% fention emulsifiable concentrate | 100 | 100 | 100 | 100 | 100 |
| | room temperature of examined day (° C) | 30.0–31.0 | 29.5–31.0 | 29.8–30.5 | 31.5–33.0 | 31.0–31.2 |

Mortality (%) in a day in opened division

| | examined date | 7/23–7/24 | 7/27–7/28 | 8/1–8/2 | 8/9–8/10 | 8/16–8/17 |
| --- | --- | --- | --- | --- | --- | --- |
| Present invention | 5% fenthion aqueous concentrate | 100 | 100 | 100 | 100 | 100 |
| | room temperature of examined day (° C) | 30.5–32.0 | 30.5–32.0 | 28.7–30.5 | 31.0–35.1 | 31.5–33.0 |

EXAMPLE 3 (Comparative Test For Toxicity Against Fish)

(1) Tested Insecticides
(a) 5% fenthion aqueous concentrate prepared in the same manner as in Example 1—(1)—(a).
(b) 5% fenthion emulsifiable concentrate prepared in the same manner as in Example 1—(1)—(b).
(2) Tested Fish: Adult of red killifish
(3) Test Method: A number of red killifish were kept for 1-10 days, among which a predetermined number of sprightly fish with almost the same length were chosen for the test. 5-10 fish were placed in an enameled container (30 cm × 20 cm × 12 cm in depth) containing 4000 ml of an insecticidal solution with a predetermined concentration. 48 hours after contact with the insecticidal solution, the number of the dead was counted. The dead fish was removed every 12 hours. The test was repeated 3 to 15 times at each concentration. During the test, the enameled container was immersed to a certain level in a concrete vessel over the top of which well water invariably overflowed so as to maintain the solution at a temperature as constant as possible.
(4) Results Mortality of red killifish 48 hours after contact with insecticidal solution

| Kind of insecticide | Present invention 5% fenthion aqueous concentrate | | | Reference 5% fenthion emulsifiable concentrate | | |
|---|---|---|---|---|---|---|
| Concentration | Number of tested fish | Number of dead fish | Mortality | Number of tested fish | Number of dead fish | Mortality |
| 3.0 ppm | 70 | 32 | 45.7 | — | — | — |
| 2.0 | 85 | 15 | 17.6 | 85 | 36 | 42.4 |
| 1.0 | 65 | 4 | 6.2 | 85 | 7 | 8.2 |
| 0.5 | 70 | 0 | 0 | 100 | 8 | 8.0 |
| 0.25 | — | — | — | 30 | 0 | 0 |

From the above results, it will be understood that the aqueous concentrate of the present invention is far lower in toxicity against fish than the known emulsifiable concentrate.

EXAMPLE 4 (Cutaneous Irritation Test)

(1) Tested Insecticide

5% fenthion aqueous concentrate prepared in the same manner as in Example 1—(1)—(a).

(2) Tested Animals

Male rabbits each having a weight of 2.0 - 3.0 kg were used, six for reference and another six for application of the testing insecticide.

(3) Application Method

The back of each rabbit was shaved in a circular shape of a radius of 2.0 -03.0 cm. 24 hours after the shaving, remaining fur was fallen off by the use of a depilatory cream. 2 days after the falling-off, 0.5 ml of the insecticide to be tested was uniformly applied to the back.

(4) Estimation

The degrees of rubefacient and scabbing formation and also of edema were estimated in accordance with the Dvaize method and were expressed in terms of marks. The intensity of the cutaneous irritation was determined from the average value of the marks obtained 24 hours and 48 hours after the application. (5) Results As will be clear from the following Table, the 5% fenthion aqueous concentrate has a final estimation mark of 0.33 and is thus found to give little cutaneous irritation action on the rabbits.

| | Kind of insecticide | Days | 1 | 2 | 3 | 4 | 5 | 6 | 7 | Final estimation marks |
|---|---|---|---|---|---|---|---|---|---|---|
| Reference | No treatment | No.1 | — | — | — | — | — | — | — | |
| | | 2 | — | — | — | — | — | — | — | |
| | | 3 | — | — | — | — | — | — | — | |
| | | 4 | — | — | — | — | — | — | — | |
| | | 5 | — | — | — | — | — | — | — | |
| | | 6 | — | — | — | — | — | — | — | |
| Present Invention | 5% fenthion aqueous concentrate | No.1 | — | — | — | — | — | — | — | 0.33 |
| | | 2 | — | — | — | — | — | — | — | |
| | | 3 | — | — | — | — | — | — | — | |
| | | 4 | — | — | — | — | — | — | — | |
| | | 5 | 2 | 1 | — | — | — | — | — | |
| | | 6 | 1 | — | — | — | — | — | — | |

EXAMPLE 5 (Preparation Of Various Aqueous Concentrate And Insecticidal Efficacy And Stability Thereof)

(1) Preparation Of Insecticides (a) Diazinon insecticide of invention 1. 5% diazinon aqueous concentrate 5 g of diazinon as an insecticidal organophosphorus compound, 14 g of polyoxyethylene diphenylmethylphenyl ether (mol number of ethylene = 12) and 0.7 g of sodium laurylsulfate as a surface active agent were mixed together. Then, 79.3 g of a mixture (having a pH of 7.0) of an aqueous 1/20 mols potassium dihydrogenphosphate solution and an aqueous 1/20 mols disodium hydrogenphosphate solution in a mixing ratio by volume of 1:2 was gradually added, as a pH adjusting agent, to the above mixture with stirring, thereby to obtain a uniform clear solution. Finally, 1 g of polyethylene glycol diglycidyl ether as a stabilizer was added to the solution to obtain 5% diazinon aqueous concentrate.

2. 5% diazinon aqueous concentrate 5.4 g of diazinon, 10 g of polyoxyethylene nonylphenol ether (having an ethylene mol number of 10) and 5 g of sodium alkylnaphthalenesulfonate were mixed together. To the mixture was added to mixture (having a pH of 7.4) of an aqueous 1/15 mols potassium dihydrogenphosphate and an aqueous 1/15 mols disodium hydrogenphosphate solution in a mixing ratio by volume of 1:4 with stirring to obtain a uniform clear solution, to which was further added 0.2 g of sodium dehydroacetate as an antifungal agent thereby obtaining 5% diazinon aqueous concentrate.

3. 20% diazinon aqueous concentrate 23 g of diazinon, 20 g of polyoxyethylene nonylphenol ether (having an ethylene mol number of 10) and 7 g of sodium alkylnaphthalenesulfonate were mixed together. To the mixture was added 47.9 g of a mixture (having a pH of 7.8) of an aqueous 1/10 mol potassium dihydrogenphosphate and an aqueous 1/20 mols borax solution in a mixing ratio by volume of 1:1 with stirring to obtain a uniform clear solution, to which were added 2 g of a stabilizer, phenyl glycidyl ether and 0.2 g of an antifungal agent to give 20% diazinon aqueous concentrate.

4. 45% diazinon aqueous concentrate 45 g of diazinon aqueous concentrate, 15 g of polyoxyethylene nonylphenol ether (having an ethylene mol number of 10), 5 g of sodium alkylnaphthalenesulfonate and 10 g of ethyl cellosolve as an organic solvent were mixed together. To the mixture was further added 21.95 g of a mixture (having a pH of 7.4) of an aqueous 1/5 mols potassium dihydrogenphosphate and disodium hydrogenphosphate in a mixing ratio by volume of 1:4 with stirring to obtain a uniform clear solution. Thereafter, 3 g of a stabilizer, phenyl glycidyl ether and 0.05 g of an antifungal agent, benzoisothiazolone, were added to the solution to obtain 45% diazinon aqueous concentrate.

(b) 10% fenitrothion aqueous concentrate 10 g of fenitrothion as an insecticidal organophosphorus compound, and 20 g of polyoxyethylene distyrylmethylphenyl ether (having an ethylene mol number of 10), were mixed together. To the mixture was gradually added, as a pH adjusting agent, 69 g of a mixture (having a pH of 6.1) of an aqueous 1/20 mols potassium dihydrogenphosphate and an aqueous 1/20 mols disodium hydrogenphosphate solution with stirring to give a uniform clear solution. Finally, 1 g of a stabilizer, polyethylene glycol diglycidyl ether, was added to the solution to obtain 10% fenitrothion aqueous concentrate.

(c) 10% ronnel aqueous concentrate 15.4 g (with a pure ronnel of 10 g) of ronnel solution (having a purity of 65% and being in the form of a methylene chloride solution) as an insecticidal organophosphorus compound and 20 g of polyoxyethylene distyrylmethylphenyl ether (having an ethylene mol number of 10) were mixed together, to which 64.6 g of water was gradually added with stirring to give a uniform clear solution. The solution was adjusted to have a pH of 5-6.

(2) Insecticidal efficacy and stability

The insecticidal efficacy and stability of the respective insecticides are shown in Table below.

Insecticidal Efficacy

| Kind of insecticide | | (a) 1 - 4 | (b) | (c) |
|---|---|---|---|---|
| | | kind of insecticidal ingredient | | |
| Tested insect | | Diazinon | Fenitrothion | Ronnel |
| Larva of Mosquitoes | Immersion method LC-50 | 0.036 ppm | 0.0098 ppm | 0.025 ppm |
| Adult of houseflies | Spray-dropping method (Nagasawa' method) KT-50 | 15 min. % 15 sec. | 29 min. % 48 sec. | 20 min. & 20 sec. |

Note: The test methods are the same as in Example 1-(2)-(a), with the abbreviations, LC-50 and KT-50, having the same meanings as defined in Example 1-(2)-(a), respectively.

Note: The test methods are the same as in Example 1—(2)—(a), with the abbreviations, LC-50 and KT-50, having the same meanings as defined in Example 1—(2)—(a), respectively.

Decomposition Rate Of Effective Component During Storage

| Kind of insecticidal component | Diazinon | | | | Fenitorthion | Ronnel |
|---|---|---|---|---|---|---|
| Storing Conditions | Kind of insecticide | | | | | |
| | 1 | 2 | 3 | 4 | | |
| Room temperature (5 - 34° C) one year | 4.0% | 2.5% | 3.0% | 4.0% | 4.2% | 2.8% |

Note: Samples were each placed in a closed glass bottle and stored in light-shielded box.

Note: Samples were each placed in a closed glass bottle and stored in light-shielded box.

I claim:

1. An aqueous insecticidal concentrate composition comprising:
   2–50% by weight O,O-diethyl-O-(2-isopropyl-4-methylpyrimidyl (6) ) thiophosphate;
   2–30% by weight of a surface active agent in an amount sufficient to render said O,O-diethyl-O-(2-isopropyl-4-methylpyrimidyl (6) ) thiophosphate soluble in water; and
   an aqueous buffer solution providing said composition with a pH ranging from 6.5 to 8.5;
   said concentrate containing at least 20% by weight water.

2. The composition as defined by claim 1, further comprising an organic solvent in an amount of less than that of said water.

3. The composition as defined by claim 2, wherein the organic solvent is a polar organic solvent in an amount of below 15% based on the total weight of the composition.

4. The composition as defined by claim 1, further comprising an antifungal agent and a stabilizer.

5. The composition as defined by claim 4, wherein said antifungal agent is selected from the group consisting of sodium dehydroacetate and 1,2-benzisothiazolone and is present in an amount of between 0.04 and 0.4% based on the weight of said composition and wherein said stabilizer is an epoxy compound and is present in an amount of between 0.3 and 3% based on the weight of said composition.

6. The composition of claim 1 wherein said buffer solution is an aqueous solution of potassium dihydrogenphosphate and disodium hydrogenphosphate, an aqueous solution of potassium dihydrogenphosphate and borax or an aqueous solution of disodium hydrogenphosphate and citric acid.

* * * * *

UNITED STATES PATENT AND TRADEMARK OFFICE
CERTIFICATE OF CORRECTION

PATENT NO. : 4,107,302            Page 1 of 3

DATED : August 15, 1978

INVENTOR(S) : HIROSHI WATANABE

It is certified that error appears in the above-identified patent and that said Letters Patent are hereby corrected as shown below:

Column 3, line 24, change "benxyl]dithiophosphate" to --benzyl]dithiophosphate--.

Column 4, line 15, delete "the" (first occurrence);
line 24, change "large" to --lapse--;
line 39, change "Any" to --An--;
line 65, change "emulsificable" to --emulsifiable--.

Column 5, line 23, change "or" to --of--;
line 25, change "skinirritating" to --skin irritating--;
line 26, change "irriation" to --irritation--;
line 42, change "mucquse" to --mucous--;
line 43, change "of" (1st occurrence) to --or--;
line 45, change "an" to --a--;
line 49, change "plant" to --plants--.

Column 6, line 13, change "toxity" to --toxicity--;
line 31, change "mthod" to --method--;
Footnote 4, (column 6) line 3 thereof, change "the stand" to --to stand--;
Under table marked "emulsion for reference" change "3.2 ml/kg" to --3.1 ml/kg--.

Column 8, table marked "Mortality (%) in a day in closed division" under heading "examined date" (line 4) change "fention" to --fenthion--;

UNITED STATES PATENT AND TRADEMARK OFFICE
CERTIFICATE OF CORRECTION

PATENT NO. : 4,107,302

DATED : August 15, 1978

INVENTOR(S) : HIROSHI WATANABE

It is certified that error appears in the above-identified patent and that said Letters Patent are hereby corrected as shown below:

Column 8, table marked "Mortality (%) in a day in opened division" is reproduced below (with corrections):

| | examined date | 7/23-7/24 | 7/27-7/28 | 8/1-8/2 | 8/9-8/10 | 8/16-8/17 |
|---|---|---|---|---|---|---|
| Present invention | 5% fenthion aqueous concentrate | 100 | 100 | 100 | 100 | 100 |
| Reference | 5% fenthion emulsifiable concentrate | 100 | 100 | 100 | 100 | 100 |
| | Room temperature of examined day (°C) | 30.5-32.0 | 30.5-32.0 | 28.7-30.5 | 31.0-35.1 | 31.5-33.0 |

Column 8, line 62, change "was" to --were--.

Column 9, line 34, change "-03.0 cm" to -- - 3.0 cm --;
  line 46, delete "(5)";
  line 47, before "Results" insert --(5)--.

UNITED STATES PATENT AND TRADEMARK OFFICE
CERTIFICATE OF CORRECTION

PATENT NO. : 4,107,302
DATED : August 15, 1978
INVENTOR(S) : HIROSHI WATANABE

It is certified that error appears in the above-identified patent and that said Letters Patent are hereby corrected as shown below:

Column 10, line 38, change "to" (second occurrence) to --a--.

Column 11, table marked "Insecticidal Efficacy" line 8 thereof, change "15 min. %" to --15 min. &--; same line, change "29 min. %" to --29 min. &--; and line 9, change "(Nagasawa'" to --(Nagasawa's --.

Column 11, delete the entire 4 lines at bottom, this being redundant but in different type.

Column 12, table marked "Decomposition Rate of Effective Component During Storage" (line 4 thereof) change "Fenitor-" to --Fenitro- --;

Column 12, lines 14 and 15, delete in their entirety since it is redundant of above two lines, but in different type.

Signed and Sealed this

Twelfth Day of June 1979

[SEAL]

Attest:

RUTH C. MASON
Attesting Officer

DONALD W. BANNER
Commissioner of Patents and Trademarks